(12) United States Patent
Burke et al.

(10) Patent No.: US 7,691,872 B2
(45) Date of Patent: Apr. 6, 2010

(54) METHODS AND COMPOSITIONS FOR OPTIMIZING BLOOD AND TISSUE STABILITY OF CAMPTOTHECIN AND OTHER ALBUMIN-BINDING THERAPEUTIC COMPOUNDS

(75) Inventors: Thomas G. Burke, Lexington, KY (US); Daniel C. Carter, Huntsville, AL (US)

(73) Assignees: University of Kentucky Research Foundation, Lexington, KY (US); New Century Pharmaceuticals, Inc., Huntsville, AL (US)

( * ) Notice: Subject to any disclaimer, the term of this patent is extended or adjusted under 35 U.S.C. 154(b) by 0 days.

(21) Appl. No.: 10/101,513

(22) Filed: Mar. 20, 2002

(65) Prior Publication Data
US 2002/0193318 A1   Dec. 19, 2002

Related U.S. Application Data

(60) Provisional application No. 60/276,908, filed on Mar. 20, 2001.

(51) Int. Cl.
  *A61K 31/44* (2006.01)
  *A61K 31/40* (2006.01)
  *A61K 31/335* (2006.01)
  *A61K 31/19* (2006.01)
(52) U.S. Cl. .......... 514/280; 514/283; 514/410; 514/453; 514/557; 514/450
(58) Field of Classification Search .......... 514/280, 514/283, 410, 453, 557, 558, 171, 211, 450; 424/450
See application file for complete search history.

(56) References Cited

U.S. PATENT DOCUMENTS 4,833,233 A   5/1989   Carter (Continued)

FOREIGN PATENT DOCUMENTS

WO   WO 9508986   *   4/1995

(Continued)

OTHER PUBLICATIONS

Hardman et al. "Goodman & Gilman's The Pharmacological Basis of Therapeutics" (9th ed, 1996) p. 51 and 57-58.*

(Continued)

*Primary Examiner*—San-ming Hui
(74) *Attorney, Agent, or Firm*—B. Aaron Schulman; Terry L. Wright; Stites & Harbison PLLC

(57) ABSTRACT

The present invention provides methods and formulations for optimizing the anti-cancer and anti-HIV activities of a camptothecin drug, including camptothecin and its related analogs including 9-aminocamptothecin and 9-nitrocamptothecin. The invention involves methodologies and formulations that limit human serum albumin-mediated reduction of the anti-cancer and anti-HIV effects of the camptothecins, and the methods and formulations provide combination therapies in which binding of the camptothecin agent to human serum albumin can be modulated by the administration of a competing agent that also binds human serum albumin. Reduced camptothecin drug binding to human serum albumin can result in elevated camptothecin free drug levels and thus improve the effectiveness of treatment regimens involving these drugs. Further agents such as methotrexate and AZT can also be used in cancer and HIV-positive patients employing camptothecin drugs.

31 Claims, 6 Drawing Sheets

U.S. PATENT DOCUMENTS

| | | | |
|---|---|---|---|
| 4,886,646 | A | 12/1989 | Carter et al. |
| 5,585,466 | A | 12/1996 | Carter |
| 5,736,156 | A | 4/1998 | Burke et al. |
| 5,786,344 | A * | 7/1998 | Ratain et al. ............... 514/100 |
| 5,834,012 | A * | 11/1998 | Perez-Soler et al. ......... 424/450 |
| 5,908,835 | A | 6/1999 | Bissery |

FOREIGN PATENT DOCUMENTS

WO        WO 9965493    * 12/1999

OTHER PUBLICATIONS

Kline, "Potentially useful combinations of chemotherapy detected in mouse tumor systems" Abstract; Database CA on STN, Chemical Abstracts Service, Cancer Chemother. Rep. Part 2, 1974, vol. 4, No. 1.

Zhang et al., "Inhibitory effects of homoharringtonine and hydroxycamptothecin in combination with other agents on cancer cell growth" Abstract; Database CA on STN, Chemical Abstracts Service, Aisa Pacific Journal of Pharmacology, 1992, vol. 7, No. 3.

Hathcock, J.N. "Metabolic Mechanisms of Drug-Nutrient Interactions" 1985, pp. 124-129, vol. 44, No. 1, Federation Proceedings, Bethesda, MD.

Guarino et al "Pharmacologic Studies of Camptothecin (NSC-100880): Distribution, Plasma Protein Binding, and Biliary Excretion", 1973, pp. 125-140, vol. 57, No. 2, Cancer Chemother. Rep.

Fleury et al "Camptothecin-binding site in human serum albumin and protein transformations induced by drug binding", Jul. 14, 1997, pp. 215-220, vol. 411, No. 2-3, Febs Letters, Elsevier, Amsterdam, Netherlands.

Burke et al "Camptothecin design and delivery approaches for elevating anti-topoisomerase I activities in vivo", 2000, pp. 36-45, Annals of the New York Academy of Sciences.

Database CA [Online] Kline Ira; "Potentially useful combinations of chemotherapy detected in mouse tumor systems", XP002959521.

* cited by examiner

METHODS AND COMPOSITIONS FOR
OPTIMIZING BLOOD AND TISSUE
STABILITY OF CAMPTOTHECIN AND
OTHER ALBUMIN-BINDING THERAPEUTIC
COMPOUNDS

CROSS-REFERENCE TO RELATED
APPLICATIONS

This application claims the benefit of U.S. Provisional Application Ser. No. 60/276,908, filed Mar. 20, 2001.

FIELD OF THE INVENTION

The invention relates in general to methods of optimizing camptothecin and other albumin-binding compounds for therapeutic use, and in particular to a method of using human serum albumin binding compounds to increase the stability and effectiveness in humans of camptothecin compounds and other albumin-binding compounds which have been shown to possess important therapeutic attributes, such as anti-cancer activity, in murine cells or other in vitro studies, but which have been far less successful in humans due to rapid lack of stability in human plasma. In addition, the invention relates to the use of human serum albumin binding compounds in conjunction with camptothecin compounds and other therapeutic agents that bind to human serum albumin in methods of treating or enhancing treatments against diseases such as cancer and/or HIV.

BACKGROUND OF THE INVENTION

Camptothecin (CPT) has been shown to inhibit the growth of a variety of animal and human tumors. Camptothecin and its related congeners display a unique mechanism of action: they stabilize the covalent binding of the enzyme topoisomerase I (topo I), an intranuclear enzyme that is overexpressed in a variety of tumor lines, to DNA. This drug/enzyme/DNA complex leads to reversible, single strand nicks that, according to the fork collision model, are converted to irreversible and lethal double strand DNA breaks during replication. Therefore, due to the mechanism of its cytotoxicity, CPT is S-phase specific, indicating that it is only toxic to cells that are undergoing DNA synthesis. Rapidly replicating cells like cancerous cells spend more time in the S-phase relative to healthy tissues. Thus, the overexpression of topo I combined with the faster rate of cell replication provide a limited basis for selectivity via which camptothecins can effect cytoxicity on cancerous cells rather than healthy host tissues. It is important to note that due to the S-phase specificity of the camptothecins, optimal inhibition of topo I requires continuous exposure to the camptothecin agent.

A closed alpha-hydroxy lactone (E) ring of CPT is an essential structural feature. An intact ring is necessary for the diffusion of the electroneutral form of the drug across membrane barriers and into cells by passive transport and, directly relevant to its in vivo anti-tumor potency, is required for the successful interaction of CPT with the topoisomerase I target. This essential lactone pharmacophore hydrolyzes under physiological conditions (pH 7 or above) and, therefore, the drug can exist in two distinct forms: 1) the biologically active, ring-closed lactone form; and 2) the biologically-inactive, ring-open carboxylate form of the parent drug. Unfortunately, under physiological conditions the drug equilibrium favors hydrolysis and, accordingly, the carboxylate form of the camptothecin drug persists. The labile nature of this alpha-hydroxy lactone pharmacophore has significantly compromised the clinical utility of the camptothecins, as continuous exposures to the active lactone form are requisite for efficacy purposes.

In human blood and tissues, the camptothecins exist in a equilibrium of active lactone form vs. inactive carboxylate form and the directionality of this equilibrium can be greatly affected by the presence of human serum albumin (HSA). Time-resolved fluorescence spectroscopic measurements taken on the intensely fluorescent camptothecin lactone and camptothecin carboxylate species have provided direct information on the differential nature of these interactions with HSA. The lactone form of camptothecin binds to HSA with moderate affinity yet the carboxylate form of camptothecin binds tightly to HSA, displaying a 150-fold enhancement in its affinity for this highly abundant serum protein. Thus, when the lactone form of camptothecin is added to a solution containing HSA, the preferential binding of the carboxylate form to HSA drives the chemical equilibrium to the right, resulting in the lactone ring hydrolyzing more rapidly and completely than when camptothecin is in an aqueous solution without HSA. In turn, this effect has negatively impacted the topoisomerase I inhibitory activity of many camptothecins and, by extension, negatively affects their clinical utility.

The important role that HSA plays in the stability of the camptothecins varies relative to drug structure. For drugs such as camptothecin and 9-aminocamptothecin, HSA functions as a biological sink for the carboxylate form. As a result, in whole human blood, 5.3% of camptothecin and only 0.5% of 9-aminocamptothecin remain in the lactone form at equilibrium. In contrast, A, B-ring substitutions of CPT, specifically at the 7- and 10-positions, can inhibit the preferential binding interactions between the camptothecin carboxylate and HSA. Accordingly, camptothecin congeners such as topotecan and SN-38, the biologically active form of the prodrug CPT-11, display lactone levels at equilibrium of 11.9% and 19.5%, respectively. Ultimately, by modulating the circulatory and tissue levels of free and active camptothecin drug, HSA can negatively impact the anti-cancer efficacy of the camptothecin agent.

The effect of serum albumins on camptothecins also differs markedly between lower vertebrates and humans and this variance has obscured the judicious selection of analogs for advancement to clinical trials. These interspecies difference have lead to significant anomalies when the data from animal models and clinical studies are compared. In particular, 9-aminocamptothecin has displayed striking activity in murine models bearing brain tumors. However, the pharmacokinetics of 9-aminocamptothecin in mice are quite different from those in humans; notably, 9-aminocamptothecin lactone levels are approximately 100-fold higher in murine blood relative to human blood. This discrepancy is due to the reduced binding of the carboxylate form of 9-aminocamptothecin to murine albumin. The logical extension of this finding is that approximately 100-fold more free lactone, which is able to cross cell membranes or the blood-brain barrier, is present in the mouse than it is in humans. The clinical relevance of this interspecies variation is underscored by a recent trial: 99 brain cancer patients were treated intravenously with 9-aminocamptothecin; the therapy was grossly ineffective (one partial responder) due to the likelihood that 99.5% of the drug was in the carboxylate form, bound to HSA and unable to transverse the blood-brain barrier.

The inherent blood instability of camptothecin has resulted in an extensive research effort to surmount the problem. Efforts to realize a blood stable camptothecin agent with potent anti-tumor activity have been primarily focused on formulation, such as liposomal preparations of the drug, and rational drug design, such as the development of the class of beta-hydroxy lactone camptothecins known as the homocamptothecins. The work described herein describes a third approach to maintaining a potent and more blood stable camptothecin congener: the modulation of camptothecin drug binding to HSA by implementing competing molecules that also bind HSA.

The camptothecins are not unique in their ability to bind albumin, as a variety of small molecules interact with this protein. A relatively large protein, 67 kD, albumin is distributed both in the plasma and in the interstitial fluid. Being one of the most abundant plasma proteins, its circulatory level ranges from 35 to 50 mg/ml (approximately 0.6 mM). The principal biological function of HSA is to maintain colloid osmotic pressure in the vascular system and to transport fatty acids and bilirubin. However, by hydrophobic and/or ionic interactions, a variety of small molecules bind tightly to albumin. Electroneutral and basic drugs may bind to albumin by hydrophobic binding interactions, and, as albumin has a net cationic charge, anionic drugs bind avidly to albumin via electrostatic interactions. Albumin possesses two well-characterized binding pockets, as well as other general binding sites. Site I is known as the warfarin binding site, which also binds drugs such as phenylbutazone, sulfonamides, phenytoin, and valproic acid. Site 11 is referred to as the diazepam site, which is also the binding site for benzodiazepines, tryptophan, ibuprofen, naproxen, octanoic acid, clofibric, iopanice, probenecid, semi-synthetic penicillins and medium chain fatty acids. Other general binding sites include sites for bilirubin, digitoxin and a variety of fatty acids. Recent x-ray crystallography and competition data obtained by the present inventors reveal that camptothecin carboxylate preferentially associates with a characterized drug binding site in subdomain IB, which overlaps with one of the main long-chain fatty acid binding sites, protoporphyrin and other drugs and compounds, although it possesses secondary affinity to binding sites I and II. Interestingly, in vivo small molecule binding to albumin is saturable at therapeutically relevant drug levels.

The ability of human serum albumin to avidly bind to a variety of small molecules offers the possibility of competitively attenuating the negative effects human serum albumin on the in vivo anti-cancer and/or anti-HIV activity of camptothecin compounds and numerous other compounds such as camptothecin that have extremely high binding affinity for human serum albumin.

However, no prior methods have recognized or attempted to deal with the problem caused by the human serum albumin binding activity, and thus methods and compositions are needed which can attenuate the negative effects of human serum albumin on the stability of compounds such as camptothecin compounds, e.g., camptothecin or 9-aminocamptothecin, and other compounds or drugs, such as protease inhibitors, which have a high affinity for human serum albumin.

SUMMARY OF THE INVENTION

It is thus an object of the present invention to utilize human serum albumin binding molecules in a method of achieving increased stability of compounds, such as camptothecin compounds, which have a high affinity for human serum albumin and which are thus generally less effective than optimal when administered in the human bloodstream.

It is also an object of the present invention to provide therapeutic methods of administering compounds such as camptothecin that have a high affinity for albumin in humans by adding a human serum albumin binding compound with the ability to bind to one or more binding sites on human serum albumin so that the compounds having high affinity for albumin can become more stable when administered and thus are far more effective than therapeutic drugs administered without such additive binding compounds.

It is still further an object of the present invention to provide a method of treating cancer wherein a camptothecin compound is administered in conjunction with an appropriate human serum albumin binding agent.

It is still further an object of the present invention to provide a method of treating HIV infection wherein a protease inhibitor is administered in conjunction with an appropriate human serum albumin binding agent.

It is even further an object of the present invention to provide a wide range of compounds which can effectively be used to increase and optimize the stability of camptothecin compounds when administered to humans.

It is even further an object of the present invention to provide a method of utilizing an agent which can bind to one or more sites on human serum albumin and yet which also has anti-tumor or tumoricidal effects and which can thus be administered in conjunction with camptothecin compounds so as to even further enhance the cancer-fighting properties of camptothecin compounds.

It is even further an object of the present invention to provide a method of utilizing an agent which can bind to one or more sites on human serum albumin and yet which also has anti-HIV abilities and which can thus be administered in conjunction with protease inhibitors so as to even further enhance the HIV-fighting properties of protease inhibitors.

It is even further an object of the present invention to provide a method of utilizing an agent which can bind to one or more sites on human serum albumin and yet which also has anti-HIV effects and which can thus be administered in conjunction with camptothecin compounds so as to even further enhance the HIV-fighting properties of camptothecin compounds.

These and other objects are achieved via the present invention which implements combination therapy consisting of competitor molecules that can bind human serum albumin (HSA) and thereby inhibit albumin binding of drugs which have a high binding affinity for human serum albumin, such as camptothecin compounds and protease inhibitors, and thus increase the effectiveness and safety of these drugs when administered to humans. This invention overcomes multiple obstacles that have been associated with therapies based on drugs such as camptothecin which have high binding affinity for human albumin. First, as a result of this binding interaction, the competitor effects elevated free camptothecin drug levels in human blood and tissues. Secondly, this invention also overcomes the negative effects of human serum albumin on the in vivo stability of some camptothecin drugs, such as camptothecin, 9-aminocamptothecin, and 9-nitrocamptothecin. For camptothecin, 9-aminocamptothecin, and 9-nitrocamptothecin, it has been demonstrated that the inactive, carboxylate form of the drug binds tightly to human serum albumin. This binding promotes a shift in the lactone/carboxylate equilibrium to favor the formation of the carboxylate form of the drug. A competitor molecule that reduces the binding of camptothecin carboxylate to human serum albumin can shift the drug equilibrium to favor re-lactonization of the camptothecin agent. As the equilibrium shifts to favor the formation of the active, lactone form of the camptothecin agent, the anti-tumor activity of the drug is preserved. Third, preservation of the electroneutral, lactone form of the camptothecin agent should enhance the cellular uptake and cellular concentration of the agent, as on the electroneutral drug species may transverse the plasma membrane. Thus, the present invention provides a method for improving camptothecin-based anti-cancer and/or anti-HIV therapies.

The competitive displacement of the camptothecin drug can occur by allosteric inhibition or by direct binding of the small molecule to the camptothecin binding pocket(s). The camptothecin agents herein can include camptothecin, 9-nitrocamptothecin, 9-aminocamptothecin, SN-38, the β-hydroxy-δ-lactone camptothecins, such as the homocamptothecins and homosilatecans, and any other camptothecin agent that physically interacts with human serum albumin either in its lactone or carboxylate form. The competing small molecule can include a diverse array of molecular entities that exhibit a binding affinity for human serum albumin. Examples include aspirin, ibuprofen, AZT, methotrexate, warfarin, and the medium chain triglycerides, such as caprylate. The patient may be administered a single competitor or a series of distinct competitors, which can be administered individually or as a mixture. The camptothecin agent and the competitor(s) can be co-administered or administered separately in order to enhance the desired therapeutic effect. The camptothecin agent and the competitor(s) can be administered orally and/or intravenously in order to enhance the desired therapeutic effect.

Another important aspect of the present invention is the use of this type of drug displacement therapy utilizing binding compounds for albumin for any drug or other beneficial compound which will be amenable to improvements in safety (by lowering the effective dose through displacement) or efficacy by allowing a higher concentration of the active principle during therapeutic treatment.

Accordingly, the present invention also is directed to the addition of an albumin-binding compound to improve the effectiveness and/or safety of drugs or therapeutic compounds which, other than camptothecin, also show binding affinity for human serum albumin. Of the top 200 pharmaceuticals as of 1999, a substantial number have high binding affinity for albumin and in most cases become at least 97% bound to albumin in the human patient. As a result, the effectiveness of these drugs can be severely limited in some cases, or far greater doses are necessary to achieve a desired result, and these inordinately higher doses almost invariably lead to greater drug side-effects which can often negate the therapeutic benefit of the drugs.

The high binding affinity in many drugs for albumin also has created problems in developing effective new drugs because many drugs are tested first in vitro or in environments outside the human body wherein the presence of human serum albumin is not provided for. As a result, many newly developed drugs work extremely well in these initial tests, but then are rendered less effective or entirely useless when administered to human patients because of their high affinity to human serum albumin which has not been accounted for. In addition to the camptothecin compounds set forth in detail herein, numerous other drugs will also be improved through introduction of albumin binding compounds in accordance with the present invention, including drugs such as protease inhibitors which have shown some initial effectiveness in anti-HIV treatment. In accordance with the present invention, the anti-HIV treatments that employ protease inhibitors with a high binding affinity for albumin will be greatly enhance when such treatments will be administered in conjunction with administration of an effective amount of the albumin-binding compounds in accordance with the present invention.

The present invention thus provides a method of utilizing the ability of human serum albumin to avidly bind to a variety of small molecules so as to competitively attenuate or eliminate negative effects of human serum albumin on the in vivo anti-cancer and/or anti-HIV capabilities of camptothecin compounds and other therapeutic compounds such as protease inhibitors which have high affinity for human serum albumin via one or more binding sites on serum albumin. Because the human serum albumin binding sites and their affinity for many small molecules have been well characterized, many of these small molecules are ideal for in vivo administration and will be useful in the present invention and can be utilized when it is necessary to target one or more particular binding sites. A number of suitable small molecules can thus be employed as human serum albumin binding competitors to effect the displacement of camptothecin drugs and compounds, either in the lactone or carboxylate form, and of other therapeutic compounds, such as protease inhibitors, which also have high binding affinity to human serum albumin. Generally, it is contemplated that treatment with albumin binding compounds in accordance with the present invention will be particularly effective with those drugs or other therapeutic compounds that exhibit about 90% or greater binding with HSA.

X-ray crystallographic experiments performed using apparatuses and methods previously described in patents such as U.S. Pat. No. 4,833,233, U.S. Pat. No. 4,886,646 and U.S. Pat. No. 5,585,466, incorporated herein by reference, have revealed the camptothecin binding sites to be overlapping with long-chain fatty acids and ibuprofen consistent with the solution chemistry.

Inhibiting the binding of the camptothecin agent to human serum albumin, or other therapeutic compounds to human serum albumin, will thus enhance free drug levels of that therapeutic compound in the blood and tissue. Given that a diverse assortment of small molecules binds to HSA, these small molecules may be administered singly or as a mixture with the camptothecin agent or other therapeutic compound to enhance their free drug levels. Moreover, via inhibiting the binding of the carboxylate form of a camptothecin drug, a shift in the equilibria occurs that favors the formation of the biologically active and electroneutral lactone species. Lastly, as many of these small molecules exhibit pharmacological activity, they may be utilized dually for their competitive binding to human serum albumin and for their desired in vivo effect. Thus, agents such as methotrexate, AZT, and a number of additional small molecules as set forth below may be used to enhance the free drug levels of camptothecin or other therapeutic drugs, such as protease inhibitors, and substantially enhance their respective biological effects in humans.

BRIEF DESCRIPTION OF THE DRAWINGS

FIG. 1 is a graphic representation of competitor binding tests between CPT and ibuprofen.

FIG. 2 is a graphic representation of competitor binding tests between hCPT and ibuprofen.

FIG. 3 is a graphic representation of competitor binding tests between SN38 and Caprylic Acid.

FIG. 4 is a graphic representation of competitor binding tests between CPT and Caprylic Acid.

FIG. 5 is a graphic representation of competitor binding tests between SN38 and HSA.

FIG. 6 is a graphic representation of competitor binding tests between hCPT and Caprylic Acid.

DETAILED DESCRIPTION OF THE PREFERRED EMBODIMENTS

For the purpose of clarity in the detailed description of the invention, the following definitions and detailed description of the invention are provided below.

Hydrolysis of the Camptothecins

Figure 1:
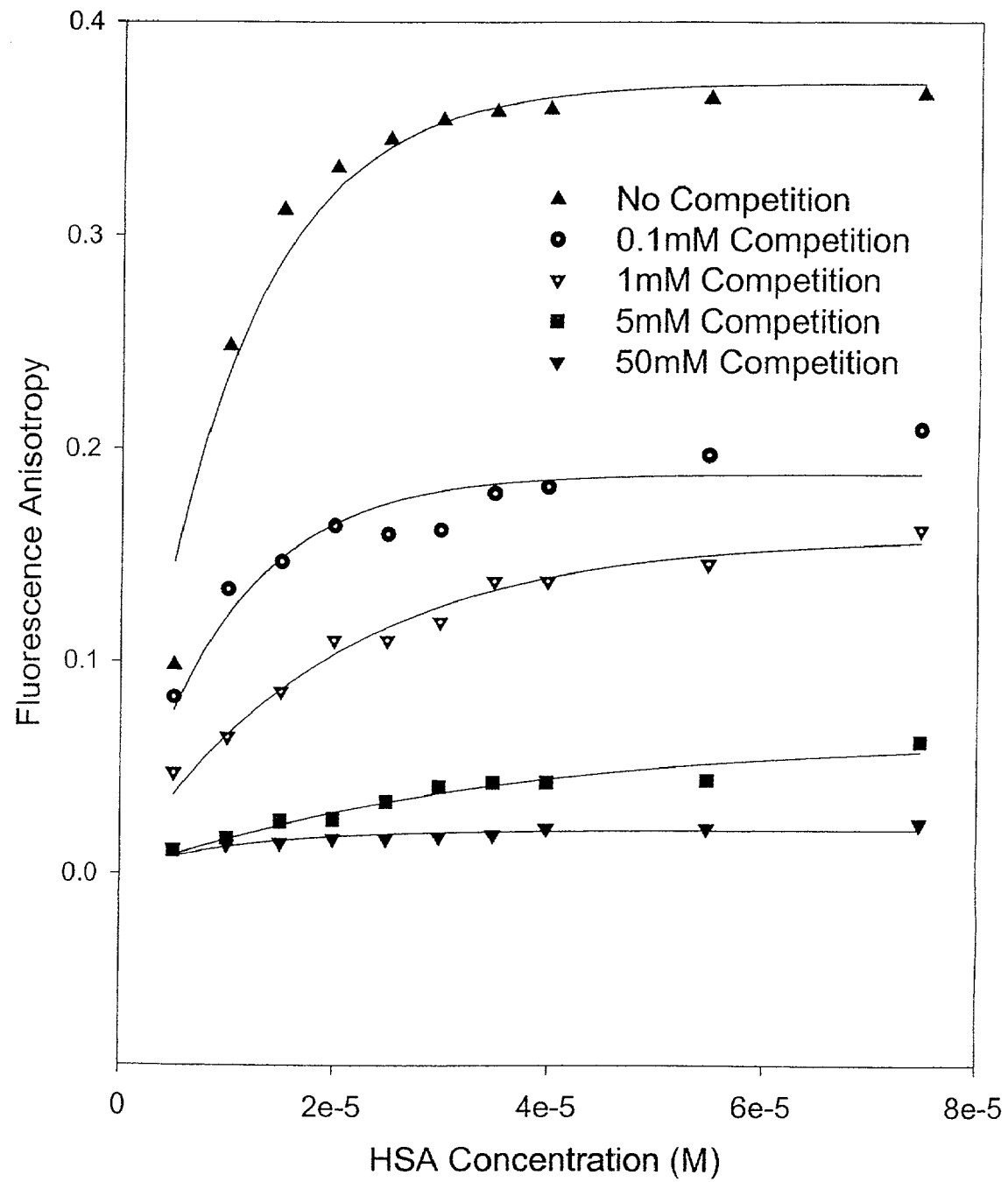
FIGS. 1-6 reflect test results with regard to camptothecin compounds (CPT) and competitor binding agents.
Figure 2:
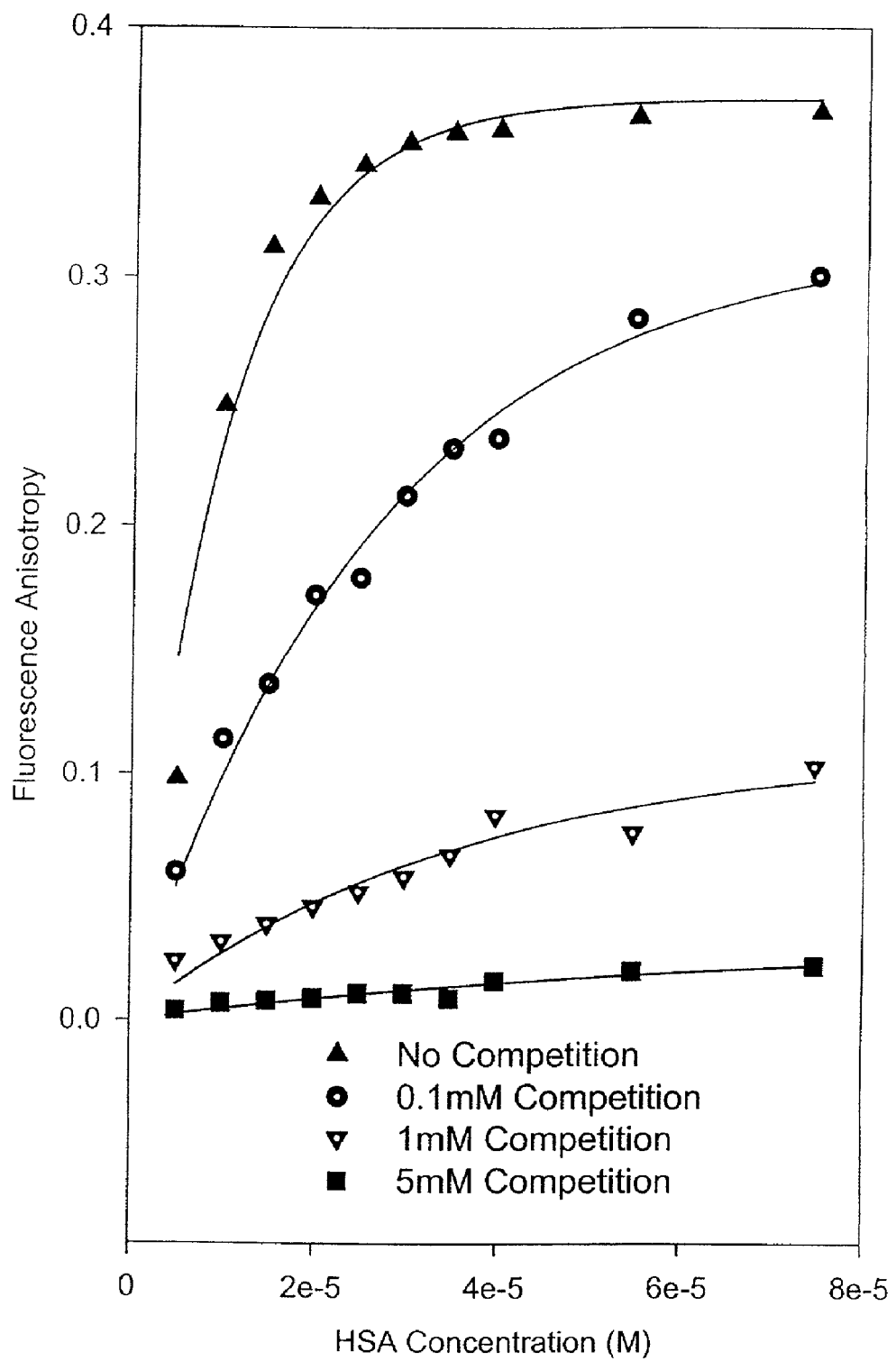
Figure 3:
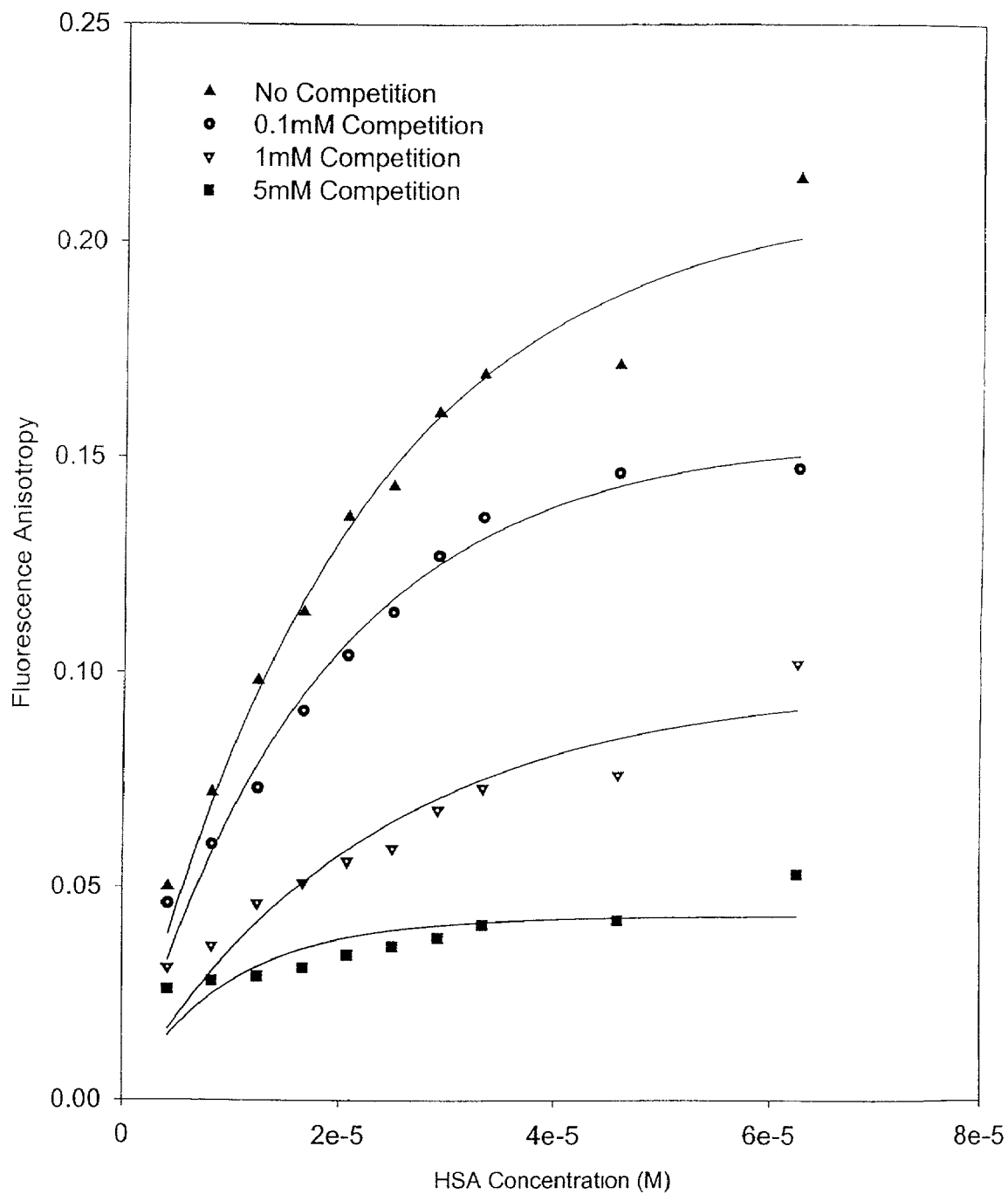
Figure 4:
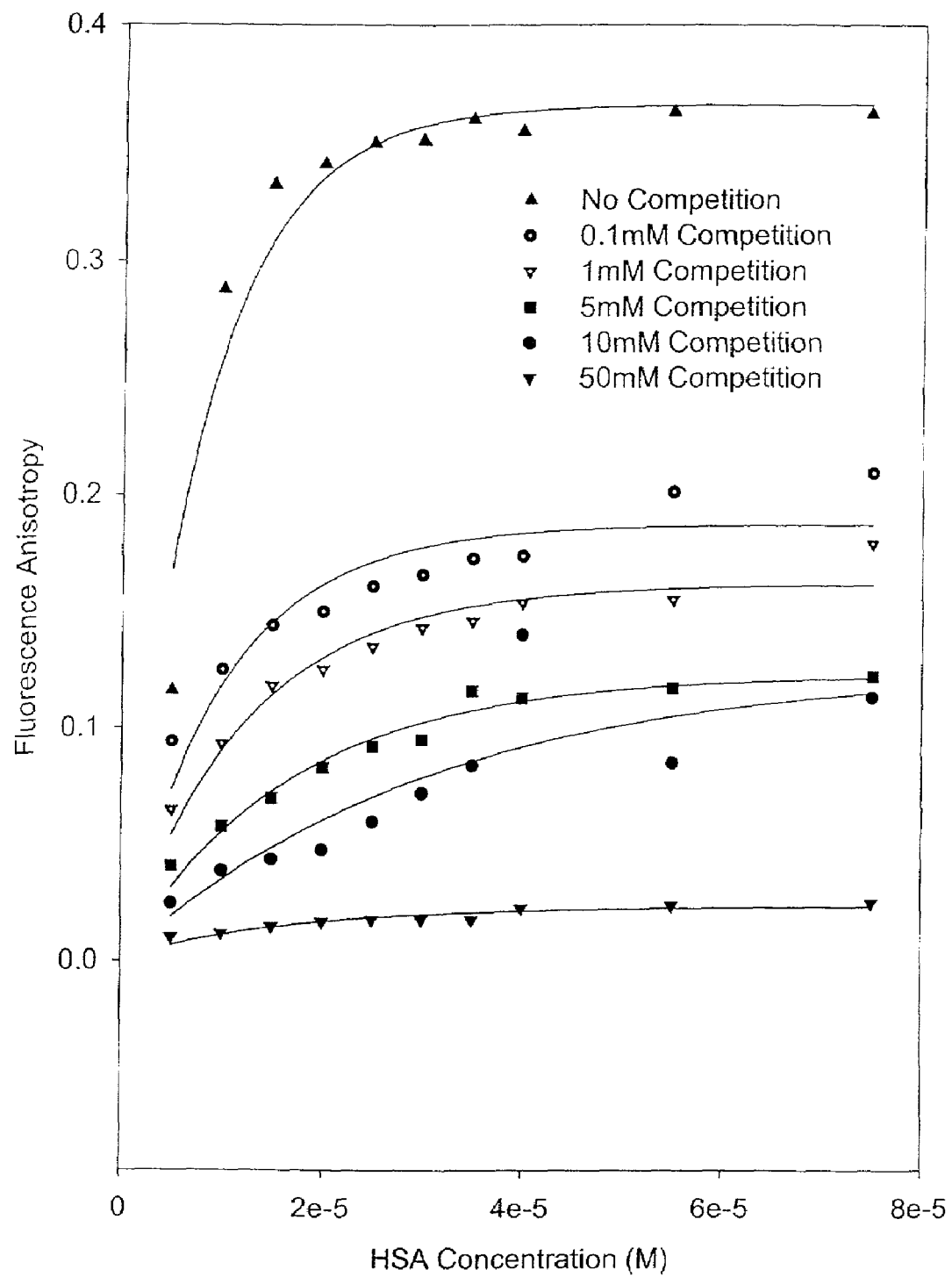
Figure 5:
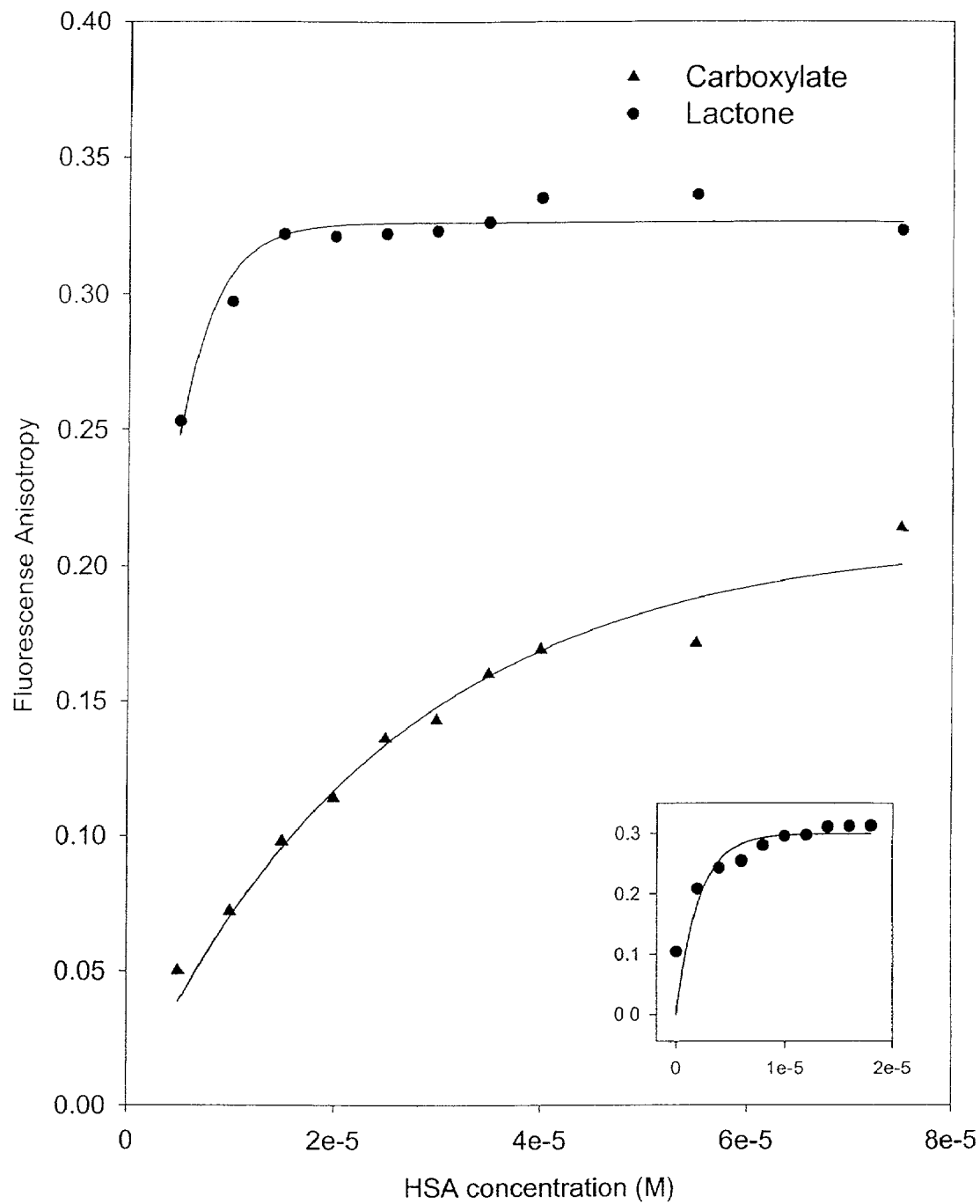
Figure 6:
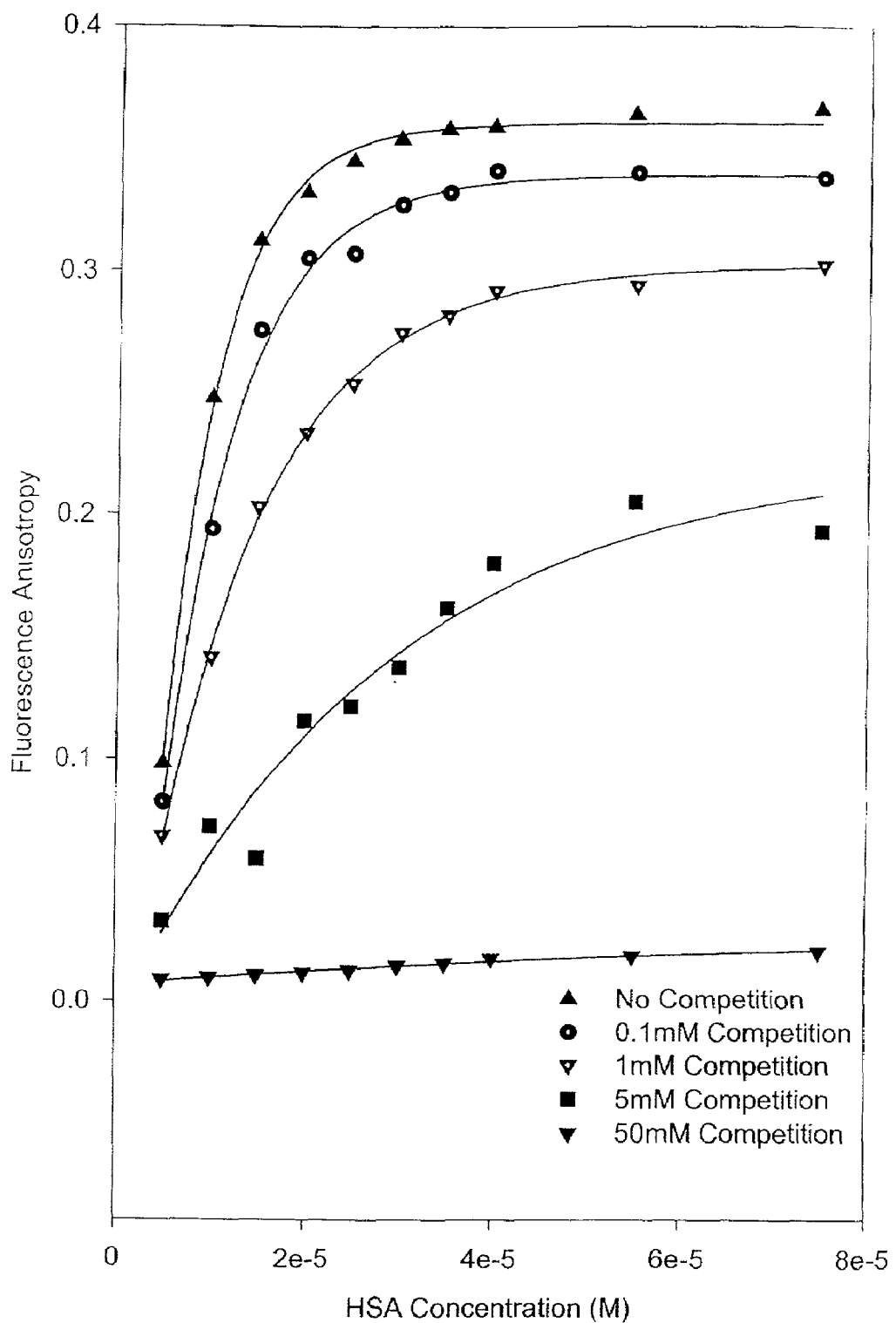

The β-hydroxy-δ-lactone members of the camptothecin class of anti-cancer drugs exhibit the following chemical equilibrium at pH 7 and above:

Figure 1: CPT Hydrolysis at Physiological pH

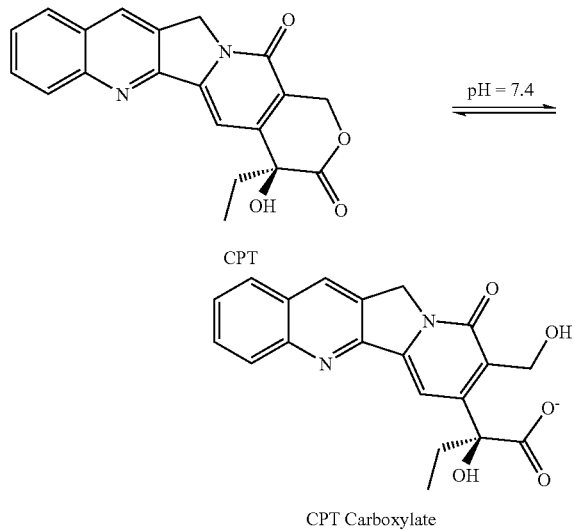

The electroneutral lactone species, as depicted on the left, represents the biologically active form of the camptothecin agent. The carboxylate species, as depicted on the right, represents the biologically inactive form of the agent. The β-hydroxy-δ-lactone camptothecins, also known as the homocamptothecins and homosilatecans, also undergo hydrolysis, however, there is no chemical equilibrium as the reaction is not reversible under normal physiological conditions. The hydrolysis of the β-hydroxy-δ-lactone camptothecins is detailed above.

HSA Binding of the Carboxylate Species

The carboxylate species of the camptothecin agent may bind HSA at specific, defined sites, as detailed by crystallographic and displacement studies, and may also bind directly to HSA at non-specific sites that have yet to be clearly defined. Binding may occur by hydrophobic and/or ionic interactions between HSA and the camptothecin carboxylate form.

HSA Binding of the Lactone Species

The lactone species of the camptothecin agent may bind HSA at specific, defined sites, as detailed by crystallographic and displacement studies, and may also bind directly to HSA at non-specific sites that have yet to be clearly defined. Binding between HSA and the camptothecin lactone form may occur by non-covalent means.

HSA Binding of the Competitor

The competitor may bind to HSA at specific, defined sites, as detailed by crystallographic and displacement studies, and may also bind HSA at non-specific sites that have yet to be clearly defined. Binding between the competitor and HSA may occur by covalent or non-covalent mechanisms.

General Definitions

Before the present compositions and methods are disclosed and described, it is to be understood that this invention is not limited to specific drugs, human serum albumin selective ligands, pharmaceutical carriers, or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. Thus, for example, reverence to a "a pharmacologically active agent" includes mixtures of two or more such ligands, and the like.

By the term "pharmacologically active agent" or "drug" as used herein is meant any chemical material or compound suitable for administration to a mammalian, preferably human, individual, which induces a desired local or systemic effect. In general, this includes: anorexics; anti-infectives such as antibiotics and antiviral agents, including many penicillins and cephalosporins; analgesics and analgesic combinations, antiarrythmics; antiarthritics; antiasthmatic agents; anticholinergics; anticonvulsants; antidiabetic agents; antidiarrheals; antihelminthics, antihistamines; anti-inflammatory agents; anti-migraine preparations; antinasuseants; antineoplastics; antiparkinsonism drugs; antipruritics; antipsychotics; antipyretics; antisense agents; antispasmodics; cardiovascular preparations including calcium channel blockers and beta-blockers such as pindolol; antihypertensives; central nervous system stimulants; cough and cold preparations, including decongestants; diuretics; gastrointestinal drugs; sympathomimetics; hormones such as estradiol and steroids; hypnotics; immunosuppressives; muscle relaxants; parasympatholytics; psychostimulatants; sedatives; tranquilizers; vasodilators including general coronary, peripheral and cerebral; xanthine derivatives.

As used herein, the term "competitor" refers to a chemical material or pharmacologically active agent suitable for administration to a mammalian, preferably human. The competitor exhibits binding affinity for serum albumin and, in general, includes: long chain fatty acids ($C_{16}$-$C_{20}$; including oleic, palmitic, linoleic, stearic, arachidonic, and palmitoleic); medium chain fatty acids ($C_6$-$C_{14}$; including caprylate or octanoate); phospholipids (lysolecithins, oleoyllysophosphatidic acid, phosphatidylcholine, phosphatidylethanolamiine); eicosanoid derivatives (leukotrienes, thromboxanes, prostaglandins A, E, F, and I); steroid hormones (cholesterol, testosterone, pregnenolone, cortisol, androsterone, indol, progesterone, estrogen); vitamin D (both monohydroxyvitamin D and dihydroxyvitamin D); bile salts (lithocholate, chenodeoxycholate, deoxycholate, ursodeoxycholate, cholate, glycolitocholate, glycochenodeoxycholate, taurochenodoxycholate, glycodeoxycholate, glycocholate, taurocholate); bilirubins (bilirubin, biliverdin, xanthobilirubin, EZ-cyclobilirubin, δ-bilirubin); porphyrins (hematin, protoporphyrin); warfarin; salicylates, ibuprofen; prednisone; iophenoxate; sulfisoxazole; phenylbutazone; oxphenylbutazone; digitoxin; indomethacin; tolbutamide; furosemide; phenytoin; chlorpropamide; chlorthiazide; the penicillins (including oxacillin, benzylpenicillin); acetotrizoate; isulfobromophthalein; deacetylcolchicine; dansylamide; dansylglutamine; dansylsarcosine; indomethacin; phenylpropazone; azobenzene derivatives; sulfobromophthalein; triiodobenzoate; benzodiazepine (including diazepam); flufenamate; iopanoate; ethacrynate; panproxen; clofibrate; L-tryptophan; N-acetyl-L-tryptophan; 6-methyltryptophan; thyroxine; 3,5,3'-L-triiodothyronine; indole propionate; kynurenine; ethacrynate; panproxen; chlorophenoxyisobutyrate; 3'azido-3'-deoxythymidine; non-steroidal anti-inflammatory agents containing ionized carboxyl groups; gossypol; meso-2,3-dimercaptosuccinic acid; captopril; N-2-mercaptoethyl-1,2-diaminopropane; disulfiramacetaminophen, dis-dichlorodiamineplatinum 9II; pyridoxal 5'-phosphate; aquocobalamin form of vitamin B12; folate; ascorbate (and its oxidation product dehydroascorbate); melatonin; α-melanotropin; gastrin; corticotropin and methotrexate.

An "effective amount" of a pharmacologically active agent is intended to mean a nontoxic but sufficient amount of the agent, such that the desired prophylactic or therapeutic effect is produced. As will be pointed out below, the exact amount of a particular agent that is required will vary from subject to subject, depending on the species, age, and general condition of the subject, the severity of the condition being treated, the particular drug used and its mode of administration, and the like. In addition, other factors, such as an assay of patient albumin levels prior to administering the therapy and adjusting the drug levels accordingly is often utilized to properly set a treatment regiment for a particular patient.

Thus, it is not possible to specify an exact "effective amount" of any particular pharmacologically active agent. However, an appropriate effective amount may be determined for any particular drug by one of ordinary skill in the art using only routine experimentation.

By the term "pharmaceutically acceptable" to describe a carrier or excipient is meant a material that is not biologically or otherwise undesirable, i.e., the material may be administered along with the selected pharmacologically active agent without causing any desirable biological effects or interacting in a deleterious manner with any of the other components of the pharmaceutical composition in which it is contained.

The term "camptothecin drug" or "camptothecin compound" is inclusive of camptothecins that contain either an E-ring α-hydroxy lactone pharmacophore or an E-ring β-hydroxy lactone pharmacophore, which includes the homocamptothecins and homosilatecans. As used herein, the camptothecin analogs 9-aminocamptothecin, 10-hydroxycamptothecin, 10,11-methylenedioxy-camptothecin, 9-nitro-10,11-methylenedioxycamptothecin, 9-chloro-10,11-methylenedioxycamptothecin, 9-amino-10,11-methylenedioxycamptothecin, 9-nitrocamptothecin, topotecan, and other analogs of camptothecin, are collectively referred to as camptothecin drugs or compounds.

DESCRIPTION OF THE INVENTION

The present invention accomplishes multiple tasks. First, administration of a HSA binding competitor elevates free camptothecin levels in blood and human tissues by inhibiting camptothecin drugs from binding to human serum albumin. Secondly, for those camptothecin drugs that bind human serum albumin in the carboxylate form, this invention induces a shift in the lactone carboxylate equilibrium that enhances in vivo drug lactone levels. Third, Enhanced free drug levels and elevated lactone levels in vivo result in greater cellular uptake and enhanced activity.

Under physiological conditions, the camptothecin drug exists in a equilibrium of the active lactone and inactive carboxylate forms. In human blood and tissues, binding of the camptothecin drug to human serum albumin can occur when said drug is either in the biologically inactive, carboxylate form or in the biologically active, lactone form. Camptothecin, 9-aminocamptothecin, and 9-nitrocamptothecin bind human serum albumin predominantly in the carboxylate form. In contrast, SN-38, the biologically active agent of the camptothecin prodrug CPT-11, binds human serum albumin in the lactone form. Binding of the camptothecin drug, whether in the carboxylate or lactone form, reduces the levels of free drug in the blood and tissue.

As described above, the present invention relates to the use of human serum albumin binding molecules which are administered in conjunction with camptothecin compounds in order to achieve greater stability in the human bloodstream and thus allow for the camptothecin compounds to be more effective when administered in human treatment regimens. The invention thus contemplates therapeutic methods, such as methods to treat diseases such as cancer or HIV, wherein camptothecin compounds are administered in humans in conjunction with a suitable human serum albumin binding compound. Even further, it is contemplated that the human serum albumin binding compound selected for use in accordance with the present invention will ideally be one that additionally enhances the effect of the free camptothecin compounds. In this regard, agents such as methotrexate, AZT, and a number of additional small molecules as set forth below may be used to enhance free camptothecin drug levels and substantially enhance their respective biological effects in humans.

The following is a list of molecules that bind human serum albumin and are thus contemplated for use in accordance with the present invention:

Long Chain Fatty Acids ($C_{16}$-$C_{20}$)
Oleic, palmitic, linoleic, stearic, arachidonic, and palmitoleic
Note for fatty acids, at pH 7 they exist as salts, and thus may more accurately be defined not as palmitic acid but as palmitate.

Medium Chain Fatty Acids ($C_6$-$C_{14}$)
Phospholipids:
Lysolecithins, oleoyllysophosphatidic acid, phosphatidylcholine, phosphatidylethanolamiine
Eicosanoid derivatives:
Leukotrienes, thromboxanes, prostaglandins A, E, F, and I
Steroid hormones:
Cholesterol, testosterone, pregnenolone, cortisol, androsterone, indol, progesterone, estrogen
Vitamin D: both monohydroxyvitamin D and dihydroxyvitamin D.
Bile Salts: Lithocholate, Chenodeoxycholate, Deoxycholate, Ursodeoxycholate, Cholate, Glycolitocholate, Glycochenodeoxycholate, Taurochenodoxycholate, Glycodeoxycholate, Glycocholate, Taurocholate
Bilirubins: bilirubin, biliverdin, xanthobilirubin, EZ-cyclobilirubin, δ-bilirubin
Gossypol (note high affinity 1.1 e-7, competes with bilirubin, antibiotic, promotes fertility)
Porphyrins: hematin, protoporphyrin
Site I Ligands (domain IIA): bilirubin, warfarin, salicylates, cyclic eicosanoids, hematin, ō-dicarboxylic medium-chain fatty acids, long-chain fatty acids, prednisone, iophenoxate (eliminated slowly due to extremely high affinity, contrast agent), salicylates, sulfisoxazole, warfarinS-, phenylbutazone, digitoxin, indomethacin, tolbutamide, furosemide, phenytoin, chlorpropamide, chlorthiazide, oxacillin, benzylpenicillin, acetotrizoate, phenol red, bromcresol green, brophenol blue, isulfobromophthalein, methyl orange, methyl red, evans blue, deacetylcolchicine, Phenol red, dansylalmide, dansylglutamine, dansylsarcosine, indomethacin, phenylpropazone, bromcresol purple, azobenzene derivatives, sulfobromophthalein, triiodobenzoate, cibacron blue, various penicillins, benzodiazepine, Site II Ligands (subdomain IIA): monocarboxylic medium-chain fatty acids ($C_6$-$C_{14}$; in particular octanoate), diazepam (the 2,3-benzodiazepines), flufenamate, iopanoate, ethacrynate, panproxen, chlorophenoxyisobutyrate (clofibrate), L-tryptophan, octanoate, thyroxine, N-Acetyl-L-tryptophan, indole propionate, kynurenine, 6-methyltryptophan, 3,5,3'-L-triiodothyronine, triiodobenzoate, ibuprofen, chloride ions, AZT (3'-azido-3'-deoxythymidine, non-steroidal anti-inflammatory agents containing ionized carboxyl groups (Li et al., 1988; Wanwimolruk et al., 1991), oxphenylbutazone Ligands at CySH-34: penicillamine, meso-2,3-dimercaptosuccinic acid, captopril (N-2-mercaptoethyl-1,2-diaminopropane, disulfiramacetaminophen, cis-dichlorodiammineplatinum9II)

Miscellaneous: pyridoxal 5'-phosphate, Aquocobalamin form of vitamin B12, folate, ascorbate and its oxidation product dehydroascorbate, melatonin, a-melanotropin, gastrin, corticotropin, calcium, nickel, magnesium, and copper It is noted that the binding of some of these molecules to human serum albumin may be readily followed by detection procedures well known in the field. For example, binding of tryptophan may easily be followed by fluorescence. In addition, different ligands may either increase or decrease the affinity of a second ligand for albumin to the extent multiple ligands are used.

In accordance with the invention, the above human serum albumin binding compounds may be utilized in conjunction with human therapies which can utilize camptothecins, and these albumin binding compounds inhibit binding of camptothecin compounds to human serum albumin present in human blood and plasma, which frees the camptothecin drug for therapeutic purposes. In addition, it is contemplated that the methods of the present invention may involve administration of a cocktail on one or more of these binders, or a single competing binding agent may be administered as needed.

It is also contemplated that these albumin binding compounds may be administered before, during, or after administration of the camptothecin agent. It is also contemplated that any camptothecin agent that binds albumin, regardless of the effect albumin has on the agent, will still be useful in accordance with the invention since one goal of the therapy is to raise the vascular and tissue levels of total free drug, and this goal will still be achieved even if albumin has an effect on the agent.

The present invention thus provides a method of utilizing the ability of human serum albumin to avidly bind to a variety of small molecules so as to competitively attenuate negative effects of human serum albumin on the in vivo camptothecin compounds' anti-cancer and anti-HIV activities. Because the human serum albumin binding site and affinity for many small molecules have been well characterized, many of these small molecules are ideal for in vivo administration and will be useful in the present invention and can be utilized when it is necessary to target particular binding sites. A number of suitable small molecules such as those described above can thus be employed as human serum albumin binding competitors to effect the displacement of camptothecin drugs and compounds, either in the lactone or carboxylate form.

In accordance with the invention, the inhibition of the binding of the camptothecin agent to human serum albumin will thus enhance free drug levels in the blood and tissue. Given that a diverse assortment of small molecules binds to HSA, these small molecules may be administered singly or as a mixture with the camptothecin agent or compound to enhance their free drug levels. Additionally, as many of these small molecules exhibit pharmacological activity, it is also contemplated they may be utilized dually for their competitive binding to human serum albumin and for their desired in vivo effect. Thus, agents such as methotrexate, AZT, and a number of additional small molecules which have therapeutic effects apart from their ability to bind human serum albumin are preferably used in accordance with the invention to even further enhance free camptothecin drug levels and substantially improve their respective biological effects in humans. These biological effects include their use as anti-cancer and/or anti-HIV agents, as well as their use in any other anti-topoisomerase I-based therapy.

The following examples are provided only to exemplify various aspects of the preferred embodiments of the present invention. It will thus be appreciated by those of skill in the art that the techniques and compositions disclosed in the examples which follow represent techniques and compositions discovered by the inventors to function well in the practice of the invention, and thus can be considered to constitute preferred modes for its practice.

However, those of skill in the art will also appreciate that the following examples are only exemplary aspects of the present invention, the scope of which is defined by the claims appended hereto, and thus many changes can be made in the specific embodiments which are disclosed and still obtain a like or similar result without departing from the spirit and scope of the invention.

EXAMPLES

Example 1

HSA/Competition Experiments by Fluorescence Spectroscopic Methods

Materials and Methods:

The camptothecin used in the experiments was obtained from Boehringer Ingelhem (Lot#95-002). Dimethyl Sulfoxide (HPLC grade, Aldrich, Milwaukee, Wis.) was used to prepare stock solutions of camptothecin at various concentrations, which were stored in the dark at −20° C. Working solutions of $1.0 \times 10^{-3}$ M camptothecin carboxylate and camptothecin lactone were prepared by diluting a stock solution of camptothecin in DMSO with PBS buffer at pH values of 10.0 and 3.0, respectively. The Sigma Chemical Co. (St. Louis, Mo.) supplied the human serum albumin (HSA) employed in the binding experiments. A $2.5 \times 10^{-3}$ M stock solution of HSA was prepared in PBS buffer at a final pH of 7.40±0.05. The concentration of the HSA was determined on a weight-to-volume basis (g/L). A Milli-Q UV PLUS purification system (Bedford, Mass.) was used to acquire high-purity water.

For the competition binding experiments, $3.0 \times 10^{-3}$ M camptothecin carboxylate and $1.0 \times 10^{-3}$ M homocamptothecin working solutions were prepared. Caprylic acid obtained from Sigma Chemical Co. (Lot#72HO473) was one of the competitive binders analyzed. Five different stock solutions of varied caprylic acid concentration were made to satisfy concentration specifications discussed below. Another competitive binder studied was Ibuprofen obtained from Sigma Chemical Co. (Lot#13HO7511). Four different stock solutions of varied ibuprofen concentration were prepared. Both caprylic acid and ibuprofen stock solutions were made-up in PBS buffer at a final pH of 7.40±0.05.

Fluorescence Spectroscopy:

Steady-state fluorescence anisotropy measurements were recorded using a SLM 9850 fluorometer interfaced with an IBM computer. The samples were excited at an excitation wavelength of 370 nm by implementing an argon ion laser. The excitation monochromator bandwidth was set to 4 nm. Fluorescence emission was isolated from scattered light by utilizing 400 nm long band-pass filters.

For the camptothecin and homocamptothecin binding experiments with HSA, fourteen test tubes of varied HSA concentration were prepared. Volumes of the $2.5 \times 10^{-3}$ M HSA stock and PBS buffer pH of 7.40±0.05 were combined in fourteen test tubes to create different HSA concentrations ranging from $0.5 \times 10^{-5}$ M to $1.8 \times 10^{-4}$ M. The test tubes were placed in a WWR Scientific Waterbath (Model 1235) set at 37° C. for approximately five minutes. Following this, the first test tube was removed and a $5.0 \times 10^{-6}$ M concentration of the drug was prepared by adding an appropriate volume of the $1.0 \times 10^{-3}$ M camptothecin or homocamptothecin (37° C) working solution to the test tube. The drug and HSA solution was immediately vortexed on a Vortex Genie 2™ from Fisher Scientific for approximately three to five seconds. Immediately after, the solution was transferred to a thermostatic (37° C.) sample cell and the anisotropy measurement was recorded. The same procedure was followed for the remaining thirteen test tubes. For each tube, the anisotropy measurement was recorded within one minute upon the addition of the drug. This short acquisition time secured that the anisotropy measurements reflected the initial form of the drug added instead of a lactone-carboxylate equilibrium form. The results of the camptothecin and homocamptothecin HSA binding experiments can be seen in the Figures.

The procedure followed for the competition binding experiments was very similar to the description above. A $3.0 \times 10^{-3}$ M camptothecin carboxylate working solution was prepared and kept at 37° C. Only ten of the fourteen test tubes described above were prepared. The HSA concentration varied from $5.0 \times 10^{-6}$ to $7.5 \times 10^{-5}$ M. The maximum HSA concentration was reduced due to background fluorescence present from the HSA. Once the HSA/PBS solutions were prepared, an appropriate volume of a competitor stock was added to each tube. The competitor concentration was identical for all ten test tubes. Caprylic acid competition concentrations of $1.0 \times 10^{-4}$ M, $1.0 \times 10^{-3}$ M, $5.0 \times 10^{-3}$ M, $1.0 \times 10^{-2}$ M and $5.0 \times 10^{-2}$ M were studied using the stock solutions discussed earlier. The same competition concentrations for Ibuprofen were studied excluding the $1.0 \times 10^{-2}$ M. Once the competitor was added, the test tubes were placed in the waterbath, like before, and the measurements were taken by employing the same technique described for the HSA binding experiment. The results for the caprylic acid and ibuprofen competition binding with camptothecin carboxylate are shown on Figures CPT/HSA and CPT: Caprylic Acid/HSA and CPT/HSA and CPT: Ibuprofen/HSA, respectively.

The homocamptothecin carboxylate competition experiments were carried out using a $1.0 \times 10^{-3}$ M homocamptothecin carboxylate working solution at 37° C. Ten test tubes were prepared using the same procedure described for the camptothecin competition experiments. Caprylic acid and ibuprofen competition concentrations of $1.0 \times 10^{-4}$ M, $1.0 \times 10^{-3}$ M, $5.0 \times 10^{-3}$ M, and $5.0 \times 10^{-2}$ M were studied.

Homocamptothecin carboxylate competition results are shown in Figures hCPT/HSA and hCPT: Caprylic Acid/HSA and hCPT/HSA and hCPT: Ibuprofen/HSA, respectively.

Background fluorescence from the HSA was detected in all of the experiments. In the camptothecin carboxylate competition experiments with caprylic acid and ibuprofen, the maximum scattered light detected was 8% and 5%, respectively. The homocamptothecin carboxylate competition experiments displayed higher values of maximum scatter equal to 13% and 15% for the caprylic acid and ibuprofen competition. In all cases, the percent of scattered light decreased with increasing competition concentration.

Example 2

Procedure of Competition Binding and Stability of 9AC, DB172, DB67 and SN38 with the Presence of Various Drugs 1. Materials Samples of 9AC, DB67, DB172 and SN38 were obtained from various sources. Human serum albumin (HSA) was purchased from Sigma Chemical (St. Louis, Mo.). Recovered human plasma was obtained from Central Kentucky Blood Center (Lexington, Ky.) and stored at −20° C. Whole human blood was obtained from a healthy male donor by drawing blood into sterile vacutainers containing heparin, to prevent clot formation. Ultrafiltration tubes were purchased from Millipore. (Centrifree; MW cutoff 30,000). Triethylamine and HPLC-grade acetonitrile was purchased from Fisher Scientific (Fair Lawn, N.J., USA). High purity water was provided by a Milli-Q UV Plus purification system (Millipore, Bedford, Mass., USA). Stock solutions of each drug were prepared in A.C.S. spectrophotometric grade dimethylsulfoxide (DMSO; Aldrich, Milwaukee, Wis., USA) at a concentration of $2 \times 10^{-3}$ M and stored in the dark at −20° C. until use. Phosphate buffered saline (PBS, pH 7.4) refers to an aqueous solution of 8 mM dibasic sodium phosphate ($Na_2HPO_4$), 1 mM potassium phosphate monobasic crystal ($KH_2PO_4$), 137 mM sodium chloride (NaCl) and 3 mM potassium chloride (KCl).

2. HPLC apparatus:

All HPLC analyses were carried out on a Waters Alliance 2690 Separations Module equipped with a Waters™ 474 Scanning fluorescence Detector, All separations were carried out on a Waters symmetry® $C_{18}$ 5 µm 3.9×150 mm column with a waters symmetry® $C_{18}$ 5 µm 3.9×20 mm guard column. For the separation of 9AC, which is higher fluorescence at low pH and the acidification of mobile phase before separation will change 9AC carboxylate form to lactone form, the postcolumn acidification was employed. The postcolumn acidification can separation carboxylate and lactone before acidify and acidify the mobile phase by pump 0.5N HCl at a flow rate 0.5 ml/min before the drug goes into the detector. A Xterra™ MS $C_{18}$ 5 µm 3.9×150 mm column (stable at low and high pH) was used for postcolumn acidifiation to stable the baseline. For the separation of 9AC, mobile phase consisted of 20% acetonitrile and 80% of an aqueous buffer containing triethylamine and acetate. The triethylamine/acetate buffer (pH 5.5) contained 2% triethylamine added to distilled, deionized water with pH adjustment to 5.5 made with concentrated acetic acid. Fluorescence excitation for 9AC was set at 380 nm and emission at 450 nm. For DB172, the mobile phase consisted of 57% acetonitrile and 43% triethylamine/acetate buffer. Excitation and emission detectors settings of 371 nm and 428 nm, respectively, were used. For DB67, the mobile phase consisted of 41% acetonitrile and 59% triethylamine/acetate buffer. Excitation and emission detectors settings of 380 nm and 560 nm, respectively, were used. For SN38, the mobile phase consisted of 25% acetonitrile and 75% triethylamine/acetate buffer. Excitation and emission detectors settings of 383 nm and 560 nm, respectively, were used. Flow rates of 1 min/ml were used in all experiments. The mobile phase was degassed by filter through a membrane filter (0.45 µm, Millipore). Fluorescence output signal was monitored and integrated using Millennium$^{32}$ Chromatography Manager software.

3. Protein Binding Studies:

Preparation of Standard Solution

A stock solution containing 2 mM of the drug of the interest in DMSO was prepared and stored at −20° C. For 9AC and DB67, an aliquot of this stock was added to PBS pH 10.0 to form 100 µM carboxylate standard solutions.

Protein Binding Studies of 9-AC Carboxylate

The present studies determined the protein binding to the carboxylate form of 9-AC. Initial experiments were run to determine the amount of 9-AC carboxylate lost during protein binding studies due to adhesion to the ultrafiltration membrane. PBS (990 µl) at pH 7.4 was spiked with 9-AC carboxylate to form 1 µM 9-AC solution. After vortexing for 30 seconds, 500 µl of the solution was transferred to an ultrafiltration device and centrifuged for 15 minutes at 4500 rpm. A 100 µl aliquot of the filtrate was added to 600 µl ice-cold methanol and vortexed. A 500 µl aliquot of the supernatant was removed and mixed with 25 µl 12 N HCl. The suspension was mixed with 1 ml of water, vortexed, and injected (100 µl) onto the HPLC. The same protocol was repeated with 100 µl total (1 µM 9-AC before ultrafiltration). The percentage recovery was obtained: the filtrate concentration divided by the total concentration.

Protein Binding of 9-AC Carboxylate to HSA (30 mg/ml), Human Plasma with or without the Presence of Various Drugs.

Protein binding studies using HSA, human plasma with and without the presence of various drugs were conducted in a similar manner. HSA were prepared with PBS (pH 7.4). A mount of different drug (phenylbutazone, ibuprofen, caprylic acid, aspirin, warfarin-Na salt, L-tryptophan) was added to HSA or human plasma to form different concentration of drug, In the test tube, 990 µl HSA solution or human plasma with or without various was spiked with 9-AC carboxylate to form 1 µM 9-AC solution. After vortexing for 30 seconds, 500 µl of the solution was transferred to an ultrafiltration device and centrifuged for 15 minutes at 4500 rpm. A 100 µl aliquot of the filtrate was added to a 600 µl ice-cold methanol, vortexed and centrifuged at 8000 rpm for 30 seconds. A 500 µl aliquot of the supernatant was removed and mixed with 25 µl 12 N HCl. Subsequently, 1 ml of water was added to the suspension and the mixture was vortexed and injected (100 µl) onto the HPLC. The same protocol was repeated with 100 µl total (1 µµM 9-AC before ultrafiltration). The total drug concentration was corrected for the apparent drug loss due to adsorption of the drug to the ultrafiltration membrane using the equation:

Corrected total concentration=determined total concentration×the percentage recovery.

The bound concentration was obtained by calculating difference: corrected total concentration minus free concentration. All experiments were run in triplicate.

Protein Binding Studies of DB67 Carboxylate

The present studies determined the protein binding to the carboxylate form of DB67. Initial experiments were run to determine the amount of DB67 carboxylate lost during protein binding studies due to adhesion to the ultrafiltration membrane. PBS (990 µl) at pH 7.4 was spiked with DB67 carboxylate to form 1 µM DB67 solution. After vortexing for 30 seconds, 500 µl of the solution was transferred to an ultrafiltration device and centrifuged for 15 minutes at 4500 rpm. A 100 µl aliquot of the filtrate was added to 600 µl ice-cold methanol and vortexed. A 500 µl aliquot of the supernatant was removed diluted with 500µl PBS (pH 12) and injected (10 µl) onto the HPLC. The same protocol was repeated with 100 µl total (1 µM DB67 before ultrafiltration). The percentage recovery was obtained: the filtrate concentration divided by the total concentration.

Protein Binding of DB67 Carboxylate to HSA (30 mg/ml), Human Plasma with or without the Presence of Caprylic Acid Protein binding studies using HSA, human plasma with and without the presence of various drugs were conducted in a similar manner. HSA were prepared with PBS (pH 7.4). A mount of caprylic acid was added to HSA or human plasma to form different concentration of drug, In the test tube, 990 µl HSA solution or human plasma with or without various was spiked with DB67 carboxylate to form 1 µM DB67 solution. After vortexing for 30 seconds, 500 µl of the solution was transferred to an ultrafiltration device and centrifuged for 15 minutes at 4500 rpm. A 100 µl aliquot of the filtrate was added to a 600 µl ice-cold methanol, vortexed and centrifuged at 8000 rpm for 30 seconds. A 500 µl aliquot of the supernatant was removed and diluted with 500 µl PBS (pH 12) and injected (10 µl) onto the HPLC. The same protocol was repeated with 100 µl total (1 µM DB67 before ultrafiltration). The total drug concentration was corrected for the apparent drug loss due to adsorption of the drug to the ultrafiltration membrane using the equation:

Corrected total concentration=determined total concentration×the percentage recovery.

The bound concentration was obtained by calculating difference: corrected total concentration minus free concentration. All experiments were run in triplicate.

Lactone Stability Studies

Lactone and Carboxylate Peak Area Ratio

A stock solution containing 2mM of interested drug was prepared and stored at −20° C. The stock solution was diluted 5-time with DMSO to form 0.4 mM stock. 2µl 0.4 mM stock was added to 798 µl DMSO to form 1 µM Lactone form, or added to 798 µl PBS pH 10.0 to form 1 µM carboxylate form, and injected onto the column. The ratio of molar fluorescence intensities of the lactone to carboxylate form (k) is calculated as following:

Lactone/carboxylate ratio (k)=average peak area of lactone/average peak area of carboxylate Stability Study of 9AC, DB67, DB172 and SN38 in Human Whole Blood, HSA or Human Plasma with or without Caprylic Acid Weigh amount of caprylic acid and added to HSA, human plasma and human whole blood to form a certain concentration of caprylic acid (1 mM, 2 mM, 10 mM, 25 mM, 50 mM and 100 mM). For HSA and human plasma, incubate the HSA or human plasma with or without caprylic acid at 37° C. and adjust pH to 7.4. For human whole blood, it will form participate with caprylic acid when adjust pH with HCl or NaOH. So, first adjust pH a little below 7.4 and then add caprylic acid to form pH 7.4 with caprylic acid in whole blood. A 5 μl 0.4 mM interest drug solution was added to 1995 μl of HSA human plasma or human whole blood that had previous been incubated at 37° C. and adjusted to pH 7.4 to form a 1 μM solution. At each respective time interval, a 150 μl volume was removed from the incubation tube and added to 600 μl of ice-cold methanol (−20° C.), vortex-mixed for 20 s and centrifuged at 4000 g for 1 min. The supernatant was directly injected onto the HPLC column immediately. Aliquots were taken and HPLC analyses was performed at times of 1, 10, 20, 30, 60, 120 and 180 minutes, respectively. The fraction of lactone form was calculated as:

Fraction of lactone=lactone area/(lactone area+carboxylate area*k), where k is the response factor defined as the ratio of molar fluorescence intensities of the lactone to carboxylate form.

In the Tables appended hereto, competition binding and stability of 9AC, DB172, DB67 and SN38 with the presence of various drugs is shown, including Table 1.1 (Protein binding of 9AC carboxylate (1 μM) in HSA and human plasma) and Table 1.2 (Protein binding of DB67 carboxylate (1 μM) in HSA and human plasma).

Competition binding and stability of 9AC, DB172, DB67 and SN38 with the presence of various drugs 1. Competition binding
1.1 Protein binding of 9AC carboxylate (1 μM) in HSA and human plasma

| Matrix | Compound added | Percent 9AC bound |
| --- | --- | --- |
| HSA (1 mg/ml) | No | 94.26 ± 0.25 |
| HSA (1 mg/ml) | Phenylbutazone (0.162 mM) | 81.52 ± 1.16 |
| HSA (1 mg/ml) | Ibuprofen (480 mM) | 0.00 ± 0.00 |
| HSA (1 mg/ml) | Caprylic acid (347 mM) | 0.00 ± 0.00 |
| HSA (30 mg/ml) | No | 100.00 ± 0.00 |
| HSA (30 mg/ml) | Ibuprofen (10 mM) | 24.82 ± 0.99 |
| HSA (30 mg/ml) | Caprylic acid (10 mM) | 83.34 ± 0.88 |
| Human plasma | No | 100.00 ± 0.00 |
| Human plasma | Phenylbutazone (0.2 mM) | 99.90 ± 0.04 |
| Human plasma | Aspirin (10 mM) | 97.98 ± 0.12 |
| Human plasma | Warfarin-Na salt (10 mM) | 86.44 ± 0.67 |
| Human plasma | L-Tryptophan (10 mM) | 99.59 ± 0.03 |
| Human plasma | Ibuprofen (100 mM) | 0.00 ± 0.00 |
| Human plasma | Ibuprofen (10 mM) | 43.06 ± 0.76 |
| Human plasma | Ibuprofen (1 mM) | 99.82 ± 0.04 |
| Human plasma | Caprylic acid (100 mM) | 0.00 ± 0.00 |
| Human plasma | Caprylic acid (80 mM) | 15.05 ± 3.17 |
| Human plasma | Caprylic acid (60 mM) | 5.14 ± 2.38 |
| Human plasma | Caprylic acid (40 mM) | 22.73 ± 1.32 |
| Human plasma | Caprylic acid (20 mM) | 74.04 ± 1.82 |
| Human plasma | Caprylic acid (10 mM) | 89.62 ± 0.18 |
| Human plasma | Caprylic acid (1 mM) | 99.86 ± 0.04 |

1.2 Protein binding of DB67 carboxylate (1 μM) in HSA and human plasma

| Matrix | Compound added | Percent DB67 bound |
| --- | --- | --- |
| HSA (30 mg/ml) | No | 99.22 ± 0.23 |
| HSA (30 mg/ml) | Caprylic acid (100 mM) | 39.09 ± 0.88 |
| HSA (30 mg/ml) | Caprylic acid (10 mM) | 75.52 ± 0.69 |
| Human plasma | No | 98.58 ± 0.09 |
| Human plasma | Caprylic acid (100 mM) | 53.39 ± 1.64 |
| Human plasma | Caprylic acid (10 mM) | 78.81 ± 0.31 |
| Human plasma | Caprylic acid (1 mM) | 96.40 ± 0.06 |

What is claimed is:

1. A method for increasing the free drug levels of a camptothecin drug that binds human serum albumin (HSA) during anti-topoisomerase I-based therapy in humans, said method comprising administering, to a human or animal patient in need of said therapy, at least one HSA-binding compound, wherein said HSA-binding compound is a phospholipid, so as to block the camptothecin binding site on HSA and thus reduce the binding of the camptothecin drug to HSA in human blood or plasma so that the free drug levels of the camptothecin drug will be increased and so that greater levels of the camptothecin will reach the drug target at the treatment site, wherein the HSA-binding compound is administered separately from the camptothecin drug.

2. The method according to claim 1, wherein the phospholipid is selected from the group consisting of lysolecithins and oleoyllysophosphatidic acid.

3. The method according to claim 1, wherein the HSA-binding compound is administered intravenously or orally.

4. The method according to claim 1, wherein the HSA-binding compound is administered before, simultaneously with, or after administration of the camptothecin drug.

5. The method according to claim 1, wherein the binding of the HSA-binding compound to HSA occurs by covalent or non-covalent means.

6. The method according to claim 1, wherein the binding of the HSA-binding compound to HSA results in the direct displacement of the camptothecin drug from its HSA binding site.

7. The method according to claim 1, wherein the binding of the HSA-binding compound to HSA results in the displacement of the camptothecin drug from its HSA binding site by allosteric inhibition.

8. The method according to claim 1 wherein the camptothecin drug is selected from the group consisting of camptothecins that contain either an E-ring α-hydroxy lactone pharmacophore or an E-ring β-hydroxy lactone pharmacophore, homocamptothecins, homosilatecans, 9-aminocamptothecin, 10-hydroxycamptothecin, 10,11-methylenedioxy-camptothecin, 9-nitro- 10,11-methylenedioxycamptothecin, 9-chloro-10,11-methylenedioxycamptothecin, 9-amino-10,11-methylenedioxy-campto-thecin, 9-nitrocamptothecin, topotecan, and combinations of the above.

9. A method for improving the free lactone levels of at least one camptothecin drug that binds in the carboxylate form to HSA during anti-topoisomerase I-based therapy, said method comprising administering, to a human or animal patient in need of said therapy, at least one HSA-binding compound, wherein said HSA-binding compound is a phospholipid, so as to block the camptothecin binding site on HSA and thus reduce the binding of the camptothecin drug to HSA in human blood or plasma so that the free lactone levels of the camptothecin drug will be increased in human blood or plasma and so that greater levels of the camptothecin will reach the drug target at the treatment site, wherein the HSA-binding compound is administered separately from the camptothecin drug.

10. The method according to claim 9, wherein the HSA-binding compound is administered intravenously or orally.

11. The method according to claim 9, wherein the HSA-binding compound is administered before, simultaneously with, or after administration of the camptothecin agent.

12. The method according to claim 9, wherein the binding of the HSA-binding compound to HSA occurs by covalent or non-covalent means.

13. The method according to claim 9, wherein the binding of the HSA-binding agent to HSA results in the direct displacement of the camptothecin drug from its HSA binding site.

14. The method according to claim 9, wherein the binding of the HSA-binding agent to HSA results in the displacement of the camptothecin drug from its HSA binding site by allosteric inhibition.

15. A method for enhancing the cellular uptake and cellular concentration of the camptothecin drug that binds to HSA during anti-topoisomerase I-based therapy, said method comprising administering, to a human or animal patient receiving said therapy, at least one HSA-binding compound, wherein said HSA-binding compound is a phospholipid, so as to block the camptothecin binding site on HSA and thus reduce the binding of the camptothecin drug to HSA in human blood or plasma so that the cellular uptake and cellular concentration of the camptothecin drug will be enhanced in human blood or plasma and so that greater levels of the camptothecin drug will reach the drug target at the treatment site, wherein the HSA-binding compound is administered separately from the camptothecin drug.

16. The method according to claim 15, wherein the HSA-binding compound is administered intravenously or orally.

17. The method according to claim 15, wherein the HSA-binding compound is administered before, simultaneously with, or after administration of the camptothecin agent.

18. A method for enhancing the therapeutic effect of a camptothecin drug that binds human serum albumin (HSA) during anti-topoisomerase I-based therapy, said method comprising administering, to a human or animal patient in need of said therapy, at least one HSA-binding compound, wherein said HSA-binding compound is a phospholipid, so as to block the camptothecin binding site on HSA and thus reduce the binding of the camptothecin drug to HSA in human blood or plasma so that the therapeutic effect of the camptothecin drug will be enhanced and so that greater levels of the camptothecin drug will reach the drug target at the treatment site, wherein the HSA-binding compound is administered separately from the camptothecin drug.

19. The method according to claim 18, wherein the HSA-binding compound is administered intravenously or orally.

20. The method according to claim 18, wherein the HSA-binding compound is administered before, simultaneously with, or after administration of the camptothecin drug.

21. The method according to claim 1, wherein the HSA-binding compound has anti-tumor or tumoricidal activity.

22. The method according to claim 1, wherein the HSA-binding compound has anti-HIV activity.

23. The method according to claim 1, wherein the HSA-binding compound that has the ability to enhance the anti-topoisomerase I-based therapy in addition to the ability to bind HSA.

24. A method for improving the effectiveness of a therapeutic treatment regimen using a camptothecin drug that binds to HSA during anti-topoisomerase I-based therapy comprising administering to a human or animal patient in need of said therapy a HSA-binding compound, wherein said HSA-binding compound is a phospholipid, so as to block the camptothecin binding site on HSA and thus reduce the binding of the camptothecin drug to HSA in human blood or plasma so that the effectiveness of the therapeutic treatment regimen of the camptothecin drug will be improved and so that greater levels of the camptothecin will reach the drug target at the treatment site, wherein the HSA binding compound is administered separately from the camptothecin drug.

25. The method according to claim 24 wherein said therapeutic treatment regimen comprises therapeutic treatment for AIDS.

26. The method according to claim 24 wherein said therapeutic treatment regimen comprises therapeutic treatment for cancer.

27. The method according to claim 1 wherein the HSA-binding compound is administered in an amount of in an amount of at least 0.1 mM.

28. The method according to claim 9 wherein the HSA-binding compound is administered in an amount of in an amount of at least 0.1 mM.

29. The method according to claim 15 wherein the HSA-binding compound is administered in an amount of in an amount of at least 0.1 mM.

30. The method according to claim 18 wherein the HSA-binding compound is administered in an amount of in an amount of at least 0.1 mM.

31. The method according to claim 24 wherein the HSA-binding compound is administered in an amount of in an amount of at least 0.1 mM.

* * * * *